United States Patent [19]

Dabroski

[11] 4,136,687

[45] Jan. 30, 1979

[54] WATER RESISTANT ORTHOPEDIC CAST

[75] Inventor: Winifred C. Dabroski, East Brunswick Township, Middlesex County, N.J.

[73] Assignee: Johnson & Johnson, New Brunswick, N.J.

[21] Appl. No.: 846,049

[22] Filed: Oct. 27, 1977

[51] Int. Cl.² .......................... A61F 13/04; C04B 11/14
[52] U.S. Cl. .................................... 128/91 R; 106/111
[58] Field of Search ........................ 106/111; 128/91 R

[56] References Cited

U.S. PATENT DOCUMENTS 3,086,953   4/1963   Nitzsche .............................. 106/111

FOREIGN PATENT DOCUMENTS 1337188   7/1963   France ..................................... 106/111

*Primary Examiner*—James Poer
*Attorney, Agent, or Firm*—Robert J. Baran

[57] ABSTRACT

The instant invention relates to a novel water resistant orthopedic bandage which includes a hardenable plaster of Paris composition, including a reactive silicone polymer supported on a flexible carrier. The amount of plaster of Paris may range from 100 to 600 grams per square yard of carrier, preferably from 396 to 425. The amount of reactive silicone may range from 0.5 to 20 parts per hundred parts plaster of Paris, preferably from 0.5 to 10, e.g. about 4 parts silicone per 100 parts plaster of Paris. The novel orthopedic bandages of the instant invention show improved water resistance throughout the curing cycle of the bandage. Also, when compared to the prior art plaster of Paris bandages the instant bandages have improved "green strength".

10 Claims, No Drawings

WATER RESISTANT ORTHOPEDIC CAST

FIELD OF INVENTION

The instant invention relates to a novel water resistant orthopedic bandage which includes a hardenable plaster of Paris composition, including a reactive silicone polymer supported on a flexible carrier. The amount of plaster of Paris may range from 100 to 600 grams per square yard of carrier, preferably from 396 to 425. The amount of reactive silicone may range from 0.5 to 20 parts per hundred parts plaster of Paris, preferably from 0.5 to 10, e.g. about 4 parts silicone per 100 parts plaster of Paris. The novel orthopedic bandages of the instant invention show improved water resistance throughout the curing cycle of the bandage. Also, when compared to the prior art plaster of Paris bandages the instant bandages have improved "green strength".

BACKGROUND OF THE PRIOR ART

The use of orthopedic bandages comprising plaster of Paris supported on a flexible material to immobilize the limb of a patient is well known in the art. Plaster of Paris has a known water sensitivity, therefore, patients wearing plaster of Paris casts must take care to avoid the rain and cannot shower. Because of this inconvenience, various improvements in the water resistance of plaster of Paris casts have been made. See, for example, U.S. Pat. Nos. 2,842,120 and 2,842,138 wherein melamine formaldehyde resin precursors have been added to plaster of Paris bandages to improve their water resistance.

Melamine formaldehyde resins have been known to cause allergic responses from the wearers of casts made from bandages of this type. Additionally, it is usually necessary to add the melamine formaldehyde precursors to the bandage in a separate step and, preferably, in an encapsulated form to preclude premature reaction. Various vinyl polymers such as polyvinyl pyrrolidone and polyvinyl acetate have also been added to improve the strength and water resistance of plaster of Paris casts (including the melamine formaldehyde resin-plaster of Paris casts noted above). See U.S. Pat. Nos. 3,671,280 and 3,649,319, respectively. Plaster of Paris casts of this type do show some improved water resistance and strength, however, further improvements in these properties would be desirable.

The addition of silicone containing materials to improve the water repellence of calcium containing masonry materials is well known in the art. In U.S. Pat. No. 2,803,561 the addition of the reaction product of a hydrolyzable, mono-hydrocarbon substituted silane and an inorganic base has been shown to improve the water repellency. There is no teaching that the addition of these silicone materials improve any property other than the water resistance of the masonry. Furthermore, there is no teaching that these materials may be used to improve the properties of plaster of Paris casts.

In U.S. Pat. No. 3,098,050, alkyl polysiloxanes which are solid materials are disclosed as improving the water repellency of masonry. These materials are said to have no effect on the setting time of masonry articles in which they are incorporated.

In U.S. Pat. No. 3,455,710 organohydrogen polysiloxane is taught as useful for waterproofing gypsum. There is no teaching of the use of these polymers for improving the water resistance of plaster of Paris orthopedic casts nor is there any teaching that the organohydrogen polysiloxane affects the cure rate of the masonry materials in any way. Furthermore, the patentee indicates that, because of the neutral or slightly acidic pH of aqueous slurries of gypsum no hydrogen liberating reaction takes place, nor would the condensation of silanol groups be expected. The patentee therefore, posits a non-reactive system.

U.S. Pat. No. 3,623,895 teaches the use of a blend of non-reactive silicones, i.e. monomethyl siloxanes and dimethyl siloxanes to waterproof masonry.

In summary, none of the above references teaches, shows or suggests the addition of reactive silicone polymers to a plaster of Paris based orthopedic bandage to improve the water resistance or the green strength of casts made therefrom.

SUMMARY OF THE INVENTION

The instant invention relates to an orthopedic bandage which comprises a hardenable plaster of Paris composition including a reactive silicone polymer supported on a flexible carrier. The novel orthopedic bandages of the instant invention show improved water resistance through out the curing cycle of the bandage. Also when compared to the prior art plaster of Paris bandages the instant bandages have improved green strength, i.e. casts made from the novel bandages of the instant invention show greater strength during the early stages of drying than casts made from the prior art plaster of Paris bandages. For the purposes of this specification, the term reactive silicone polymer means that the reactive silicone polymer is capable of reacting to form high molecular weight silicone polymers at the conditions obtained during the activating and drying of the plaster of Paris.

The reactive silicone polymer is a relatively low molecular weight polymer having a polymer backbone comprising repeating Si—O units and functional groups attached thereto which are capable of co-reaction to form high molecular weight polymers having the polysiloxane backbone. Suitable functional groups include H, OH, Cl Br, F, I, $NH_2$, amino, olefin, carboxyl, and sulfhydryl radicals which may be attached directly to the polysiloxane backbone, i.e. to the silicon atom, or through intervening hydrocarbyl radicals.

It is desirable, in the orthopedic bandage of the instant invention, that the self-reacting silicone form a three dimensional structure upon reacting. Therefore, a major portion of the self-reacting silicone polymer should be tri-functional or greater. It is within the scope of the instant invention to utilize a blend of silicon polymers having different molecular weights and/or functional groups, provided the functional groups are capable of coreaction. Catalysts may also be used to promote the rate of reaction of the reactive silicone polymer.

A preferred reactive silicone polymer comprises a blend of a disilanol represented by the general structure

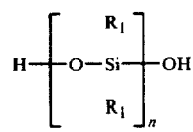

and a silane functional crosslinking agent represented by the general structure

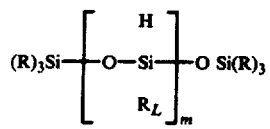

wherein n is an integer of from about 100 to 5000, m is an integer of from about 1 to 50 and $R_1$ is a hydrocarbyl radical or an oxyhydrocarbyl radical such as a methyl, ethyl or phenyl radical, but preferably a methyl radical is selected because of the improved water resistance imparted thereby.

The molar ratio of the disilanol and the silane as well as the values for n and m will be adjusted to provide a three dimensional structure upon reaction. For example, molar ratios of from 1:9 to 9:1 disilanol to silane may be used. Selecting the proper ratio and values for n and m is within the skill of the art. To maximize water repellancy the value for m is selected to as to provide a disilanol having a viscosity of up to about 50,000; preferably 2,000 to 5,000 Centipoise as measured at 25° C. The value for n is most preferably from 10 to 40.

A catalyst is preferably added to the above reactive silicone polymer to promote reaction during the activation and drying of the plaster of Paris. Such catalysts include organo metallic compounds such as metal octoates and maphthenates. The catalyst may be an organotin compound having the general structure

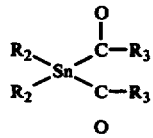

wherein $R_2$ may be selected from the group consisting of methyl, butyl and octyl radicals and $R_3$ may be selected from the group consisting of methyl, heptyl and undecyl radicals.

Other suitable catalysts include the octoates and naphthenates of zinc, iron, lead, calcium, manganese and cobalt.

Another less preferred reactive silicone comprises a vinyl functional poly dimethyl-siloxane such as

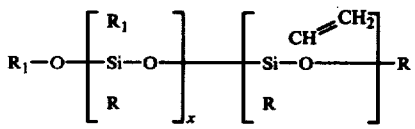

wherein y is an integer of from 1 to about 2000, in place of the disilanol described above. This system may be cured with a noble metal complex catalyst such as a platinum catalyst.

The novel orthopedic bandages may include from 100 to 600 grams plaster of Paris per square yard of flexible carrier and an amount of reactive silicone ranging from 0.5 to 20 parts per hundred plaster of Paris. To insure proper wetting of the bandage the amount of reactive silicone is preferably from 0.5 to 10, e.g. about 4 parts per hundred plaster of Paris.

The flexible support may be gauze, woven fiberglass, reticulated polyurethane, etc.

Other components which may be included in the novel orthopedic bandages of this invention include binders such as polyvinyl acetate, dextrin, etc.

It may also be desirable to improve the hand or working properties of the instant bandages such as by adding creaminess agents, e.g. high molecular weight polyethyleneoxides.

To vary the rate of setting of the plaster of Paris accelerators such as $K_2SO_4$, etc. and retarders such as $NHP_3BO_3$ may also be included in the finished bandage.

All of the above materials can be incorporated into the instant novel orthopedic bandage by methods known in the art. For example, all of the above ingredients can be dissolved in water or a suitable solvent, slurried with the plaster of Paris, and the slurry coated on to the flexible carrier. It is preferred, however, to add the reactive silicone to the slurry just prior to the plaster of Paris, or alternatively the reactive silicone may be sprayed onto the dry plaster of Paris, prior to the above slurrying step. The slurry may be coated onto the flexible support by using a reverse roll coater.

As previously noted, the hardenable plaster of Paris composition utilized in the bandages of the instant invention may be coated onto the flexible support in a single step in comparison to the compositions used to prepare the prior art, water resistant plaster of Paris casts wherein the water resistance agent has to be added in a separate step. However, it may be desirable to add the reactive silicone, in a separate step, by spraying onto the flexible support after it has been coated with the above hardenable plaster of Paris composition.

After coating the slurry onto the flexible support, the bandage may be dried at temperatures of from about 50 to 250° C. The dried bandages may then be cut, packaged, etc. All of the above steps which are used in the preparation of the instant bandages are known in the art, therefore, more detailed description is not necessary for the skilled artisan.

The instant novel bandages also show unexpected differences in the rate of setting when compared to the prior art plaster of Paris bandages.

As noted above, the use of accelerators such as potassium sulfate, is well known in the prior art processes for preparing plaster of Paris bandages. Accelerators are added to the slurry of the components making up the hardenable composition to regulate the set time of the bandage. The amount of accelerator added is adjusted to give as uniform and as fast a set time as possible with the particular batch of materials used to make up the hardening composition. It has been found that the set time will increase after storage of the prior art bandages, therefore excess $K_2SO_4$ is added to the plaster of Paris slurry to give an initial set time of 4–5 minutes knowing that this initial set time will increase to about 7 minutes after one month's storage at standard conditions. The set time on the prior art plaster of Paris bandages will increase thereafter, albeit at a lower rate.

The instant orthopedic bandages show the exact opposite behavior. The initial set time may be from 6 to 7 minutes, with a lesser amount (for example, one half) of the $K_2SO_4$ accelerator. After storage for one day at normal conditions the set time will decrease to 4.5 minutes and thereafter will level off and remain at 4 minutes for months thereafter. Besides the obvious advantage of using less accelerator in the instant bandages, the physician will thus be assured of a uniform set time, even if using bandages having different storage histories.

Additional K$_2$SO$_4$ may be added to the instant novel bandages to lower the initial set time to about 4.5 minutes. In this manner, a fairly uniform set time throughout the entire storage history of the bandage may be obtained.

The following examples are specific embodiments of the instant invention. There is no intention, however, to limit the claims thereto, since many variations will be readily apparent to those skilled in the art.

EXAMPLE 1

Comparison between Prior Art Plaster of Paris Bandages and the Bandages of the Instant Invention The following solutions were prepared for testing:

Master Solution (A)
 Water 114.0 lb. : starch solution
 Dextrin 24.0 lb. : premixed
 Water 875.4 lb.
 Potassium sulfate 7.0 lb.
 30% ammonium hydroxide 16.8 lb.
 Boric acid 12.0 lb.
 Gelva TS 30 30.0 lbs.

(A polyvinyl Acetate Emulsion available from Monsanto. Co.)

Master Solution (B)
 Water 114.0 lb.
 Dextrin 24.0 lb.
 Water 875.4 lb.
 Potassium sulfate 7.0 lb.
 30% ammonium hydroxide 16.8 lb.
 Boric acid 12.0 lb.
 Gelva TS 30 30.0 lbs.
 36.0 lbs. of Carefree 30, a reactive silicone polymer dispersion available from Jersey State Chemical Co., A Division of Sybron Corp. This dispersion includes 30% solids and the polymer is characterized as having reactive hydrogen and hydroxyl radicals.

Master Solution (C)
 Water 114.0 lb.
 Dextrin 24.0 lb.
 Water 875.4 lb.
 Potassium slfte 7.0 lb.
 30% ammonium hydroxide 16.8 lb.
 Boric acid 12.0 lb.
 Gelva TS 30 30.0 lbs.
 36 lbs. of Carefree 30
 2.0 lbs. Stannous Octoate Master solutions A, B and C were each added to plaster of Paris to form a slurry in the ratio of 57 lbs. master solution to 100 lbs. of plaster of Paris. This slurry was coated on 32 × 28 cotton gauze at a weight of 398 gms/yd$^2$. The coated cloth was dried in a 2-zone oven at temperatures of 250° F and 350° F. for two minutes. Samples were cut in 5 yd. × 4 in. bandages, rewet in 70° F water and wrapped in a 2 in. diameter pipe. Crush tests were conducted on a Dillon crush tester after various lengths of time. The results were as follows:

| Sample | ½ hr. | 1 hr. | 24 hr. | 24 hr. Wet* |
|---|---|---|---|---|
| A | 400 lbs. | 400 lbs. | 570 lbs. | 220 lbs. |
| B | 450 lbs. | 600 lbs. | 650 lbs. | 560 lbs. |

-continued

| Sample | ½ hr. | 1 hr. | 24 hr. | 24 hr. Wet* |
|---|---|---|---|---|
| C | 575 lbs. | 700 lbs. | 750 lbs. | 600 lbs. |

*Samples were immersed in 70° F water for two minutes prior to crushing.

The improved water resistance of the bandages of the instant invention, both with and without a catalyst as compared to the prior art plaster of Paris bandages, is apparent. The improvement in 'green strength' i.e. the initially developed strength, over the prior art plaster of Paris should also be noted.

EXAMPLE 2

Comparison Between Reactive and Non-Reactive Silicones

Master Solution (D)
 Same as master solution A with 36.0 lbs Syloff 22 added.

Master Solution (E)
 Same as master solution A except 36.0 lbs. of Syloff 1171 added.
 These materials are reactive silicone polymers available from Dow Corning Co. as dispersions in water. The polymers are characterized as having reactive hydrogen and hdyroxyl groups.

Master Solution (F)
 Same as master solution A except 36.0 lbs. of SWS 108 added. This material is a non-reactive silicone polymer available from SWS Silicones Corp. Adrian, Michigan Master Solution (G)
 Same as master solution A except 36.0 lbs. of SWS 231 added. This material is a non-reactive silicone polymer available from SWS Silicones Corp., Adrian, Michigan Master solutions A, D, E, F and G were slurried with plaster of Paris in a ratio of 57 lbs. of master solution to 100 lbs. of plaster of Paris. The slurries were coated on 32 ×0 28 gauze at a weight of 52-54 gms. per yd. × 4 and dried at 350° F for 2-3 minutes. These samples were wrapped on a 1" diameter bar and dry and wet crush tests, utilizing the Dillon crush tester carried out. Prior to crushing the samples were dried for four days. The wet crush test was carried out after a 2 minute soaking of the dried samples in 70° F water.

| Sample | | Dry Crush | Wet Crush |
|---|---|---|---|
| | A (control | 105 lb. | 50 lb. |
| (reactive) | D (Syloff 22) | 230 lb. | 130 lb. |
| (reactive) | E (Syloff 1171) | 215 lb. | 110 lb. |
| (non-react.) | F (SWS 108) | 180 lb. | 50 lb. |
| (non-react.) | G (SWS 231) | 190 lb. | 40 lb. |

The improved strength (wet and dry) of casts made from the bandages including reactive silicones as compared to non-reactive silicones is readily apparent. Note also that although the non-reactive silicones improve the dry strength there is no effect whatsoever on the wet strength.

EXAMPLE 3

Comparison of Prior art Plaster of Paris Bandage with Bandage of the Invention

Master Solution (H) - Control
  Water 130.9 lbs.: starch solutions
  Dextrin 27.0 lbs.: premixed
  Water 875.4 lbs.
  Potassium Sulfate 7.0 lbs.
  30% Ammonium Hydroxide 16.8 lbs.
  Boric Acid 8.4 lbs.
  Gelva TS 30 30.0 lbs.

Master Solution (I)
  Master solution H including, in addition 36.0 lbs. of Carefree 30 and 20 lbs. of catalyst SG a zinc catalyst available from Jersey State Chemical Co. as a 30% solids mixture.
  Additionally, $K_2SO_4$ was most added to give the set time shown below.
  Master solutions H and I were each mixed with plaster of Paris to form a slurry in the ratio of 57 lbs. master solution to 100 lbs. of plaster of Paris. This slurry was coated on 32 × 28 gauze at a weight of 410/gm/yd² and dried at 475° F for 35 seconds. The samples were tested for strength (units given are in pounds) by means of the above procedure.

| Sample | ½ hr. | 1 hr. | 24 hrs. Dry | 24 hrs. Wet* | 3 day | 7 days Dry | 7 days Wet* | Set Time |
|---|---|---|---|---|---|---|---|---|
| H | 450 | 490 | 580 | 250 | 900 | 875 | 400 | 4.8 min. |
| I | 550 | 600 | 700 | 420 | 1150 | 1000 | 800 | 4.0 min. |

*two min. soak in 70° F.

Note the improvement in wet and dry strength of the instant novel bandage over the entire course of drying. Note, also the improvement in set time as compared to the prior art bandage.

EXAMPLE 4

To Test the Effectiveness of Increasing Amounts of Reactive Silicone, the following Experiments were run:

Master Solution (J)
  Same as master solution B with 90.0 lbs. Carefree 30 instead of 36.0 lbs.

Master Solution (K)
  Same as master solution B with 180 lbs. of Carefree 30 instead of 36.0 lbs.

Master Solution (L)
  Same as master solution B with 360 lbs. Carefree 30 instead of 36.0 lbs.

Master Solutions A, B, J, K and L were mixed with plaster of Paris to form a slurry in the ratio of 57 lbs. to 100 lbs. plaster of Paris. The slurries were coated on 32 × 28 gauze at a weight of 402 gms/yd² and dried in a 2 zone oven 250° F and 350° F for 2 minutes. The dried bandages were made into 5 yd. × 4" samples, said samples were dipped in 70° F water to initiate the hardening, and the dipped samples were wrapped on 2" pipe. After drying, for various times, the crush strength was tested on the Dillon crush tester.

| Sample | ½ hr. | 1 hr. | 24 hr. dry | 24 hr. wet | (2 min. Soak 70° F Water) |
|---|---|---|---|---|---|
| A (control) | 200* | 280 | 400 | 200 | |
| B | 250 | 300 | 450 | 390 | |
| J | 230 | 300 | 480 | 390 | |
| K | 250 | 340 | 500 | 400 | |
| L | 300 | 350 | 530 | 450 | |

*lbs.

EXAMPLE 5

The following example demonostrates the unexpected finding that the set time of plaster of Paris bandages including reactive silicones increase with the time while the opposite is true with the prior art plaster of Paris bandages.

| Sample | Set Times Initial | 1 day | 2 weeks | 1 month |
|---|---|---|---|---|
| (H) | 4.0 | 4.5 | 5.6 | 6.7 |
| (I)* | 6.5 | 4.5 | 4.0 | 4.0 |

*Post added $K_2SO_4$ was omitted to demonstrate the difference in set time between the instant novel bandages and the prior art. As stated above the addition of extra $K_2SO_4$ will stabilize the set time over the storage history of the bandage.

*Post added $K_2SO_4$ was omitted to demonstrate the difference in set time between the instant novel bandages and the prior art. As stated above the addition of extra $K_2SO_4$ will stabilize the set time over the storage history of the bandage.

The set time is measured on 5 wraps of activated plaster of Paris bandage using the Vicat Plunger having a head weight of 300 gms and fitted with a No. 4 Sharp sewing needle. The plunger is placed on the sample. The time at which the needle does not penetrate the 5 wraps is considered the set time. Note that the sample with silicone did not have the extra potassium sulfate accelerator added while the sample without silicone included extra.

EXAMPLE 6

The Effect of Increasing the Amount of Catalyst for the Reactive Silicone

Master Solution (M)
  Master solution B with 1.8 lbs. of catalyst SG added after the Carefree 30.

Master Solution (N)
  Master solution B with 5.4 lbs. catalyst SG added instead of 1.8 lbs.

Master Solution (O)
  Master solution B with 10.8 lbs. of catalyst SG after the Carefree 30.

| Sample | 3 day Dry | 3 day Wet | (2 min. soak 70° water) |
|---|---|---|---|
| B | 167 lbs. | 50 lbs. | |
| M | 200 lbs. | 100 lbs. | |
| N | 190 lbs. | 100 lbs. | |
| O | 212 lbs. | 110 lbs. | |

What is is: :
  1. A water resistant orthopedic bandage having improved water resistance, green strength and dry crush strength which includes a hardenable plaster of Paris composition, including a reactive silicone polymer supported on a flexible carrier.

2. The bandage of claim 1 wherein the plaster of Paris ranges from 100 to 600 grams per square yard of carrier.

3. The bandage of claim 2 wherein said plaster of Paris ranges from 396 to 425 grams per square yard of carrier.

4. The bandage of claim 2 wherein said reactive silicone ranges from 0.5 to 10 parts per hundred parts plaster of Paris.

5. A bandage of claim 1 wherein said reactive silicone polymer comprising a blend of a disilanol represented by the general structure:

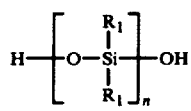

and a silane functional crosslinking agent represented by the general structure:

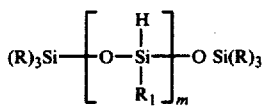

6. The bandage of claim 5 wherein said polymer composition additionally includes a catalyst to promote reaction during the activation and drying of the plaster of Paris wherein such catalyst is selected from the group consisting of organo metallic compounds.

7. The bandage of claim 5 wherein the molar ratio of the disoilanol and the silane will vary from 1 to 9 to 9 to 1.

8. The bandage of claim 5 wherein the amount of reactive silicone is from 0.5 to 10 parts per hundred parts plaster of Paris.

9. The bandage of claim 6 wherein said catalyst is selected from the group consisting of the octoates and naphthenates of zinc, iron, lead, calcium, manganese and cobalt.

10. The bandage of claim 6 wherein said catalyst is an organo-tin compound having the general structure:

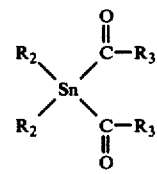

wherein $R_2$ may be selected from the group consisting of methyl, butyl and octyl radicals and $R_3$ may be selected from the group consisting of methyl, heptyl and undecyl radicals.

* * * * *